United States Patent
Schwab et al.

(10) Patent No.: US 9,795,498 B2
(45) Date of Patent: Oct. 24, 2017

(54) INTRAGASTRIC BALLOON FOR TREATING OBESITY

(71) Applicant: Apollo Endosurgery, Inc., Austin, TX (US)

(72) Inventors: Justin J. Schwab, Santa Barbara, CA (US); Zachary P. Dominguez, Santa Barbara, CA (US); Joseph S. Raven, Tigard, OR (US); Mitchell H. Babkes, Santa Clarita, CA (US); Christopher S. Mudd, Keller, TX (US); Tiago Bertolote, Geneva (CH)

(73) Assignee: APOLLO ENDOSURGERY US, INC., Austin, TX (US)

( * ) Notice: Subject to any disclaimer, the term of this patent is extended or adjusted under 35 U.S.C. 154(b) by 196 days.

(21) Appl. No.: 14/433,752

(22) PCT Filed: Oct. 3, 2013

(86) PCT No.: PCT/US2013/063276
§ 371 (c)(1),
(2) Date: Apr. 6, 2015

(87) PCT Pub. No.: WO2014/055766
PCT Pub. Date: Apr. 10, 2014

(65) Prior Publication Data
US 2015/0272761 A1   Oct. 1, 2015
US 2016/0331568 A9   Nov. 17, 2016

Related U.S. Application Data

(63) Continuation of application No. 13/645,026, filed on Oct. 4, 2012, now Pat. No. 8,870,966.

(51) Int. Cl.
A61M 29/00   (2006.01)
A61F 5/00   (2006.01)

(52) U.S. Cl.
CPC ........... *A61F 5/003* (2013.01); *A61F 5/0033* (2013.01); *A61F 5/0036* (2013.01)

(58) Field of Classification Search
CPC .... A61F 2/04; A61F 5/00; A61F 5/003; A61F 5/0036; A61F 5/0033; A61F 2/00; A61F 2/06; A61F 2/24; A61M 29/00
See application file for complete search history.

(56) References Cited

U.S. PATENT DOCUMENTS 1,702,974 A   2/1929   Macdonald
2,087,604 A   7/1937   Mosher
(Continued)

FOREIGN PATENT DOCUMENTS

CN   1250382 A   4/2000
CN   1367670 A   9/2002
(Continued)

OTHER PUBLICATIONS

'Living With the Bib/BioEnterics Intragastric Balloon Program,' Inamed Health; 1-10 Patient Information Brochure; pp.; May 1, 2005.
(Continued)

*Primary Examiner* — Victor Nguyen
(74) *Attorney, Agent, or Firm* — Gordon & Jacobson, P.C.

(57) ABSTRACT

A transorally implanted intragastric balloon or treating obesity and for weight control including a variable size balloon with one or interconnected regions acting to exert a pressure on the stomach, to provide a stomach volume occupying effect, and/or to anchor the balloon within the stomach.

14 Claims, 6 Drawing Sheets

(56) References Cited

U.S. PATENT DOCUMENTS

| | | |
|---|---|---|
| 2,163,048 A | 6/1939 | McKee |
| 2,619,138 A | 11/1952 | Marler |
| 3,667,081 A | 6/1972 | Burger |
| 3,719,973 A | 3/1973 | Bell |
| 3,840,018 A | 10/1974 | Heifetz |
| 3,919,724 A | 11/1975 | Sanders |
| 4,118,805 A | 10/1978 | Reimels |
| 4,364,379 A | 12/1982 | Finney |
| 4,416,267 A | 11/1983 | Garren |
| 4,430,392 A | 2/1984 | Kelley |
| 4,485,805 A | 12/1984 | Foster |
| 4,545,367 A | 10/1985 | Tucci |
| 4,586,501 A | 5/1986 | Claracq |
| 4,592,355 A | 6/1986 | Antebi |
| 4,598,699 A | 7/1986 | Garren |
| 4,607,618 A | 8/1986 | Angelchik |
| 4,636,213 A | 1/1987 | Pakiam |
| 4,648,383 A | 3/1987 | Angelchik |
| 4,694,827 A | 9/1987 | Weiner |
| 4,723,547 A | 2/1988 | Kullas |
| 4,739,758 A | 4/1988 | Lai |
| 4,773,432 A | 9/1988 | Rydell |
| 4,774,956 A | 10/1988 | Kruse |
| 4,844,068 A | 7/1989 | Arata |
| 4,881,939 A | 11/1989 | Newman |
| 4,899,747 A | 2/1990 | Garren |
| 4,925,446 A | 5/1990 | Garay |
| 4,930,535 A | 6/1990 | Rinehold |
| 4,950,258 A | 8/1990 | Kawai |
| 4,969,899 A | 11/1990 | Cox |
| 5,074,868 A | 12/1991 | Kuzmak |
| 5,084,061 A | 1/1992 | Gau |
| 5,211,371 A | 5/1993 | Coffee |
| 5,226,429 A | 7/1993 | Kuzmak |
| 5,255,690 A | 10/1993 | Keith |
| 5,259,399 A | 11/1993 | Brown |
| 5,289,817 A | 3/1994 | Williams |
| 5,308,324 A | 5/1994 | Hammerslag |
| 5,312,343 A | 5/1994 | Krog |
| 5,449,368 A | 9/1995 | Kuzmak |
| 5,514,176 A | 5/1996 | Bosley |
| 5,527,340 A | 6/1996 | Vogel |
| 5,540,701 A | 7/1996 | Sharkey |
| 5,547,458 A | 8/1996 | Ortiz |
| 5,601,604 A | 2/1997 | Vincent |
| 5,658,298 A | 8/1997 | Vincent |
| 5,693,014 A | 12/1997 | Abele |
| 5,725,507 A | 3/1998 | Petrick |
| 5,748,200 A | 5/1998 | Funahashi |
| 5,776,160 A | 7/1998 | Pasricha |
| 5,819,749 A | 10/1998 | Lee |
| 5,820,584 A | 10/1998 | Crabb |
| RE36,176 E | 3/1999 | Kuzmak |
| 5,938,669 A | 8/1999 | Klaiber |
| 6,074,341 A | 6/2000 | Anderson |
| 6,102,678 A | 8/2000 | Peclat |
| 6,102,897 A | 8/2000 | Lang |
| 6,102,922 A | 8/2000 | Jakobsson |
| 6,152,922 A | 11/2000 | Ouchi |
| 6,183,492 B1 | 2/2001 | Hart |
| 6,264,700 B1 | 7/2001 | Kilcoyne |
| 6,290,575 B1 | 9/2001 | Shipp |
| 6,322,538 B1 | 11/2001 | Elbert |
| 6,450,946 B1 | 9/2002 | Forsell |
| 6,454,699 B1 | 9/2002 | Forsell |
| 6,454,785 B2 | 9/2002 | DeHoyosGarza |
| 6,464,628 B1 | 10/2002 | Forsell |
| 6,470,892 B1 | 10/2002 | Forsell |
| 6,503,264 B1 | 1/2003 | Birk |
| 6,511,490 B2 | 1/2003 | Robert |
| 6,540,789 B1 | 4/2003 | Silverman |
| 6,547,801 B1 | 4/2003 | Dargent |
| 6,579,301 B1 | 6/2003 | Bales |
| 6,629,776 B2 | 10/2003 | Bell |
| 6,675,809 B2 | 1/2004 | Stack |
| 6,682,473 B1 | 1/2004 | Matsuura |
| 6,733,512 B2 | 5/2004 | McGhan |
| 6,733,513 B2 | 5/2004 | Boyle |
| 6,746,460 B2 | 6/2004 | Gannoe |
| 6,776,783 B1 | 8/2004 | Frantzen |
| 6,840,257 B2 | 1/2005 | Dario |
| 6,845,776 B2 | 1/2005 | Stack |
| 6,905,471 B2 | 6/2005 | Leivseth |
| 6,960,233 B1 | 11/2005 | Berg |
| 6,981,978 B2 | 1/2006 | Gannoe |
| 6,981,980 B2 | 1/2006 | Sampson |
| 6,994,095 B2 | 2/2006 | Burnett |
| 7,008,419 B2 | 3/2006 | Shadduck |
| 7,020,531 B1 | 3/2006 | Colliou |
| 7,033,384 B2 | 4/2006 | Gannoe |
| 7,037,344 B2 | 5/2006 | Kagan |
| 7,056,305 B2 | 6/2006 | GarzaAlvarez |
| 7,090,699 B2 | 8/2006 | Geitz |
| 7,214,233 B2 | 5/2007 | Gannoe |
| 7,220,237 B2 | 5/2007 | Gannoe |
| 7,220,284 B2 | 5/2007 | Kagan |
| 7,223,277 B2 | 5/2007 | DeLegge |
| 7,320,696 B2 | 1/2008 | Gazi |
| 7,347,875 B2 | 3/2008 | Levine |
| 7,354,454 B2 | 4/2008 | Stack |
| 7,476,256 B2 | 1/2009 | Meade |
| 7,510,559 B2 | 3/2009 | Deem |
| 7,608,114 B2 | 10/2009 | Levine |
| 7,628,442 B1 | 12/2009 | Spencer |
| 7,682,330 B2 | 3/2010 | Meade |
| 7,695,446 B2 | 4/2010 | Levine |
| 7,699,863 B2 | 4/2010 | Marco |
| 7,753,870 B2 | 7/2010 | Demarais |
| 7,771,382 B2 | 8/2010 | Levine |
| 7,794,447 B2 | 9/2010 | Dann |
| 7,815,589 B2 | 10/2010 | Meade |
| 7,837,643 B2 | 11/2010 | Levine |
| 7,841,503 B2 | 11/2010 | Sonnenschein |
| 7,883,525 B2 | 2/2011 | DeLegge |
| 7,931,693 B2 | 4/2011 | Binmoeller |
| 7,981,162 B2 | 7/2011 | Stack |
| 8,029,455 B2 | 10/2011 | Stack |
| 8,032,223 B2 | 10/2011 | Imran |
| 8,075,582 B2 | 12/2011 | Lointier |
| 8,162,969 B2 | 4/2012 | Brister |
| 8,187,297 B2 | 5/2012 | Makower |
| 8,216,266 B2 | 7/2012 | Hively |
| 2002/0019577 A1 | 2/2002 | Arabia |
| 2002/0055757 A1 | 5/2002 | Torre |
| 2002/0095181 A1 | 7/2002 | Beyar |
| 2002/0139208 A1 | 10/2002 | Yatskov |
| 2002/0183782 A1 | 12/2002 | Tsugita |
| 2003/0040804 A1* | 2/2003 | Stack ............ A61F 2/04 623/23.7 |
| 2003/0045896 A1 | 3/2003 | Murphy |
| 2003/0073880 A1 | 4/2003 | Polsky |
| 2003/0074054 A1 | 4/2003 | Duerig |
| 2003/0100822 A1 | 5/2003 | Lew |
| 2003/0106761 A1 | 6/2003 | Taylor |
| 2003/0109935 A1 | 6/2003 | Geitz |
| 2003/0144575 A1 | 7/2003 | Forsell |
| 2003/0153905 A1 | 8/2003 | Edwards |
| 2003/0158570 A1 | 8/2003 | Ferrazzi |
| 2004/0044357 A1 | 3/2004 | Gannoe |
| 2004/0092892 A1 | 5/2004 | Kagan |
| 2004/0117031 A1 | 6/2004 | Stack |
| 2004/0122452 A1 | 6/2004 | Deem |
| 2004/0122453 A1 | 6/2004 | Deem |
| 2004/0143342 A1 | 7/2004 | Stack |
| 2004/0148034 A1 | 7/2004 | Kagan |
| 2004/0172142 A1 | 9/2004 | Stack |
| 2004/0186503 A1 | 9/2004 | DeLegge |
| 2005/0033332 A1 | 2/2005 | Burnett |
| 2005/0049718 A1 | 3/2005 | Dann |
| 2005/0055039 A1 | 3/2005 | Burnett |
| 2005/0085923 A1 | 4/2005 | Levine |
| 2005/0096692 A1 | 5/2005 | Linder |
| 2005/0110280 A1 | 5/2005 | Guy |
| 2005/0131485 A1 | 6/2005 | Knudson |

(56) References Cited

U.S. PATENT DOCUMENTS

| | | |
|---|---|---|
| 2005/0190070 A1 | 9/2005 | Rudduck |
| 2005/0192614 A1 | 9/2005 | Binmoeller |
| 2005/0192615 A1 | 9/2005 | Torre |
| 2005/0197714 A1 | 9/2005 | Sayet |
| 2005/0228504 A1 | 10/2005 | Demarais |
| 2005/0240279 A1 | 10/2005 | Kagan |
| 2005/0250979 A1 | 11/2005 | Coe |
| 2005/0256533 A1 | 11/2005 | Roth |
| 2005/0261711 A1 | 11/2005 | Okada |
| 2005/0267595 A1 | 12/2005 | Chen |
| 2005/0267596 A1 | 12/2005 | Chen |
| 2005/0273060 A1 | 12/2005 | Levy |
| 2005/0277975 A1 | 12/2005 | Saadat |
| 2006/0020278 A1 | 1/2006 | Burnett |
| 2006/0025799 A1 | 2/2006 | Basu |
| 2006/0069403 A1 | 3/2006 | Shalon |
| 2006/0106288 A1 | 5/2006 | Roth |
| 2006/0142700 A1 | 6/2006 | Sobelman |
| 2006/0178691 A1 | 8/2006 | Binmoeller |
| 2006/0190019 A1 | 8/2006 | Gannoe |
| 2006/0217762 A1 | 9/2006 | Maahs |
| 2006/0229702 A1 | 10/2006 | Agnew |
| 2006/0252983 A1 | 11/2006 | Lembo |
| 2007/0010864 A1 | 1/2007 | Dann |
| 2007/0016262 A1 | 1/2007 | Gross |
| 2007/0021761 A1 | 1/2007 | Phillips |
| 2007/0078476 A1 | 4/2007 | Hull |
| 2007/0083224 A1 | 4/2007 | Hively |
| 2007/0100368 A1 | 5/2007 | Quijano |
| 2007/0118168 A1 | 5/2007 | Lointier |
| 2007/0135803 A1 | 6/2007 | Belson |
| 2007/0135829 A1 | 6/2007 | Paganon |
| 2007/0147170 A1 | 6/2007 | Hood |
| 2007/0149994 A1 | 6/2007 | Sosnowski |
| 2007/0156013 A1 | 7/2007 | Birk |
| 2007/0156248 A1 | 7/2007 | Marco |
| 2007/0173881 A1 | 7/2007 | Birk |
| 2007/0185374 A1 | 8/2007 | Kick |
| 2007/0239284 A1 | 10/2007 | Skerven |
| 2007/0250020 A1 | 10/2007 | Kim |
| 2007/0265598 A1 | 11/2007 | Karasik |
| 2007/0276428 A1 | 11/2007 | Haller |
| 2007/0288033 A1 | 12/2007 | Murature |
| 2007/0293716 A1 | 12/2007 | Baker |
| 2008/0015618 A1 | 1/2008 | Sonnenschein |
| 2008/0058840 A1 | 3/2008 | Albrecht |
| 2008/0058887 A1 | 3/2008 | Griffin |
| 2008/0065122 A1 | 3/2008 | Stack |
| 2008/0071305 A1 | 3/2008 | DeLegge |
| 2008/0097513 A1 | 4/2008 | Kaji |
| 2008/0167606 A1 | 7/2008 | Dann |
| 2008/0172079 A1 | 7/2008 | Birk |
| 2008/0208240 A1 | 8/2008 | Paz |
| 2008/0208241 A1 | 8/2008 | Weiner |
| 2008/0221595 A1 | 9/2008 | Surti |
| 2008/0228205 A1 | 9/2008 | Sharkey |
| 2008/0234718 A1 | 9/2008 | Paganon |
| 2008/0234834 A1 | 9/2008 | Meade |
| 2008/0243071 A1 | 10/2008 | Quijano |
| 2008/0243166 A1 | 10/2008 | Paganon |
| 2008/0243221 A1 | 10/2008 | Arcand |
| 2008/0249635 A1 | 10/2008 | Weitzner |
| 2008/0255601 A1 | 10/2008 | Birk |
| 2008/0255678 A1 | 10/2008 | Cully |
| 2008/0262529 A1 | 10/2008 | Jacques |
| 2008/0306506 A1 | 12/2008 | Leatherman |
| 2009/0012553 A1 | 1/2009 | Swain |
| 2009/0082644 A1 | 3/2009 | Li |
| 2009/0093767 A1 | 4/2009 | Kelleher |
| 2009/0093837 A1 | 4/2009 | Dillon |
| 2009/0131968 A1 | 5/2009 | Birk |
| 2009/0132031 A1 | 5/2009 | Cook |
| 2009/0149879 A1 | 6/2009 | Dillon |
| 2009/0171382 A1 | 7/2009 | Dillon |
| 2009/0177215 A1 | 7/2009 | Stack |
| 2009/0198210 A1 | 8/2009 | Burnett |
| 2009/0216337 A1 | 8/2009 | Egan |
| 2009/0259246 A1 | 10/2009 | Eskaros |
| 2009/0275973 A1 | 11/2009 | Chen |
| 2009/0287231 A1 | 11/2009 | Brooks |
| 2009/0299327 A1 | 12/2009 | Tilson |
| 2009/0299486 A1 | 12/2009 | Shohat |
| 2009/0312597 A1 | 12/2009 | Bar |
| 2010/0030017 A1 | 2/2010 | Baker |
| 2010/0049224 A1 | 2/2010 | Vargas |
| 2010/0081991 A1 | 4/2010 | Swisher |
| 2010/0082047 A1 | 4/2010 | Cosgrove |
| 2010/0087843 A1 | 4/2010 | Bertolote |
| 2010/0100079 A1 | 4/2010 | Berkcan |
| 2010/0100115 A1 | 4/2010 | Soetermans |
| 2010/0121371 A1 | 5/2010 | Brooks |
| 2010/0168782 A1 | 7/2010 | Hancock |
| 2010/0168783 A1 | 7/2010 | Murature |
| 2010/0174307 A1 | 7/2010 | Birk |
| 2010/0198249 A1 | 8/2010 | Sabliere |
| 2010/0234937 A1 | 9/2010 | Wang |
| 2010/0249822 A1 | 9/2010 | Nihalani |
| 2010/0249825 A1 | 9/2010 | Nihalani |
| 2010/0256775 A1 | 10/2010 | Belhe |
| 2010/0256776 A1 | 10/2010 | Levine |
| 2010/0261390 A1 | 10/2010 | Gardner |
| 2010/0274194 A1 | 10/2010 | Sobelman |
| 2010/0286628 A1 | 11/2010 | Gross |
| 2010/0305590 A1 | 12/2010 | Holmes |
| 2010/0331756 A1 | 12/2010 | Meade |
| 2010/0332000 A1 | 12/2010 | Forsell |
| 2011/0009897 A1 | 1/2011 | Forsell |
| 2011/0106113 A1 | 5/2011 | Tavakkolizadeh |
| 2011/0307075 A1 | 12/2011 | Sharma |
| 2012/0022561 A1 | 1/2012 | Forsell |
| 2012/0095483 A1 | 4/2012 | Babkes |
| 2012/0221037 A1 | 8/2012 | Birk |

FOREIGN PATENT DOCUMENTS

| | | |
|---|---|---|
| DE | 8804765 U1 | 5/1989 |
| DE | 102007025312 A1 | 11/2008 |
| EP | 1396242 | 3/2004 |
| EP | 1396243 | 3/2004 |
| EP | 1397998 A1 | 3/2004 |
| EP | 1774929 A2 | 4/2007 |
| EP | 2095798 | 9/2009 |
| FR | 2797181 | 2/2001 |
| FR | 2823663 | 10/2002 |
| FR | 2852821 A1 | 10/2004 |
| FR | 2855744 | 12/2004 |
| FR | 2892297 A1 | 4/2007 |
| FR | 2941617 A1 | 8/2010 |
| GB | 2086792 A | 5/1982 |
| JP | 63264078 | 10/1988 |
| JP | S63279854 A | 11/1988 |
| JP | 1049572 A | 2/1989 |
| WO | 8800027 A1 | 1/1988 |
| WO | 0015158 | 3/2000 |
| WO | 0032092 | 6/2000 |
| WO | 0110359 | 2/2001 |
| WO | 0149245 | 7/2001 |
| WO | 0166166 A2 | 9/2001 |
| WO | 0235980 A2 | 5/2002 |
| WO | 03055419 A1 | 7/2003 |
| WO | 03105732 | 12/2003 |
| WO | 2004019671 A2 | 3/2004 |
| WO | 2005007231 A1 | 1/2005 |
| WO | 2005094257 A2 | 10/2005 |
| WO | 2005097012 A2 | 10/2005 |
| WO | 2005110280 A2 | 11/2005 |
| WO | 2006020370 | 2/2006 |
| WO | 2006044640 A1 | 4/2006 |
| WO | 2006063593 A2 | 6/2006 |
| WO | 2006090018 A1 | 8/2006 |
| WO | 2006111961 A2 | 10/2006 |
| WO | 2006118744 A1 | 11/2006 |
| WO | 2007027812 A2 | 3/2007 |
| WO | 2007053556 A1 | 5/2007 |

(56) References Cited

FOREIGN PATENT DOCUMENTS

| WO | 2007076021 A2 | 7/2007 |
|---|---|---|
| WO | 2007092390 A2 | 8/2007 |
| WO | 2007110866 A2 | 10/2007 |
| WO | 2008101048 A2 | 8/2008 |
| WO | 2008112894 A1 | 9/2008 |
| WO | 2008132745 A2 | 11/2008 |
| WO | 2010042062 A1 | 4/2010 |
| WO | 2010074712 A2 | 7/2010 |
| WO | 2010087757 A1 | 8/2010 |
| WO | 2010117641 A2 | 10/2010 |

OTHER PUBLICATIONS

Bib Bioenterics Intragastric Balloon Program, 'Take Control of Your Weight and Your Life/The Solution for You,' Inamed Health, pp. 1-2; Jan. 19, 2004.
Bib Bioenterics Intragastric Balloon Program, 'Taking the Next Step/Take Control of Your Weight and Your Life,' Inamed Health, pp. 1-9; Apr. 29, 2004.
Bib Data Sheet Directions for Use, 'BioEnterics Intragastric Balloon System,' Inamed Health, 1-12 pp.; Rev 03, Feb. 2005.
Chaudhri; 'Can Gut Hormones Control Appetite and Prevent Obesity?' Diabetes Care; V. 31; Supp 2; pp. S284-S289; Feb. 2008.
Greenough et al.; 'Untangling the Effects of Hunger, Anxiety, and Nausea on Energy Intake During Intravenous Cholecystokinin Octapeptide (CCK-8) Infusion'; Physiology & Behavior; V. 65, No. 2; pp. 303-310; 1998.
Houpt; 'Gastrointestinal Factors in Hunger and Satiety'; Neurosci. and Behav. Rev.; V. 6; pp. 145-164; 1982.
Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.
Baggio et al. 'Biology of Integrins: GLP-1 and GIP'; Gastroenterology; V. 132; pp. 2131-2157; 2007.
Berne et al; 'Physiology'; V. 5; pp. 55-57, 210, 428, 540, 554, 579, 584, 591; 2004.
Boulant et al.; 'Cholecystokinin in Transient Lower Oesophageal Sphincter Relation Due to Gastric Distension in Humans'; Gut; V. 40; pp. 575-581; 1997.
Bradjewin et al; 'Dose Ranging Study of the Effects of Cholecystokinin in Healthy Volunteers'; J. Psychiatr. Neurosci.; V. 16 (2); pp. 91-95; 1991.
Cohen et al.; 'Oxyntomodulin Suppresses Appetite and Reduces Food Intake in Humans'; J. Clin. Endocrinol. Metab.; V. 88; No. 10; pp. 4696-4701; 2003.
Dakin et al.; 'Oxyntomodulin Inhibits Food Intake in the Rat'; Endocrinology; V. 142; No. 10; pp. 4244-4250; 2001.
Dakin et al.; 'Peripheral Oxyntomodulin Reduces Food Intake and Body Weight gain in Rats'; Endocrinology; V. 145; No. 6; pp. 2687-2695; Jun. 2004.
Davison; 'Activation of Vagal-Gastric Mechanoreceptors by Cholecystokinin'; Proc. West. Pharmocol. Soc; V. 29; pp. 363-366; 1986.
Ekblad et al.; 'Distribution of Pancreatic Peptide and Peptide-YY'; Peptides; V. 23; pp. 251-261;2002.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Kissileff et al.; 'Peptides that Regulate Food Intake: Cholecystokinin and Stomach Distension Combine to Reduce Food Intake in Humans'; Am. J. Physiol. Regul. Integr. Comp. Physiol.; V. 285; pp. 992-998; 2003.
Naslund et al. 'Pranidal subcutaneous injections of glucagon-like peptide-1 cause weight loss in obese human subjects'; British Journal of Nutrition; V. 91; pp. 439-446; 2004.
Renshaw et al. 'Peptide YY: A Potential Therapy for Obesity'; Current Drug Targets; V. 6; pp. 171-179; 2005.
Weiner et al.; "Preparation of Extremely Obese Patients for Laparoscopic Gastric Banding by Gastric Balloon Therapy"; Obesity Surgery; V. 9, pp. 261-264, 1999.
Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.

\* cited by examiner

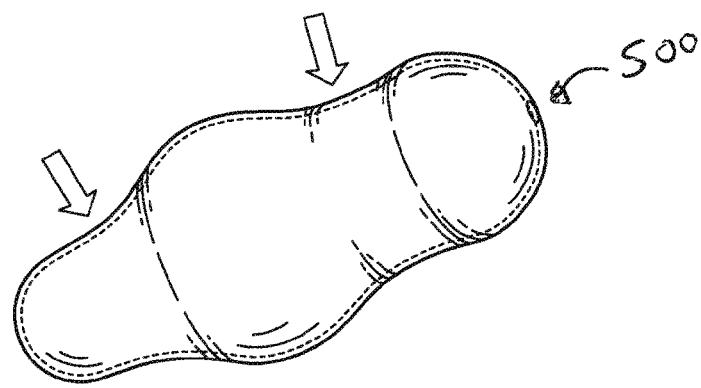
FIG. 5
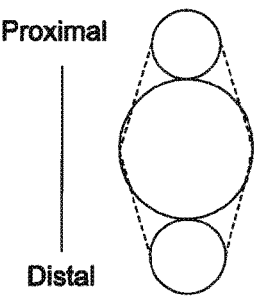 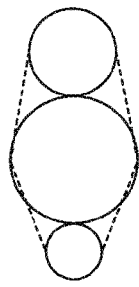 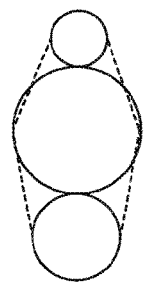 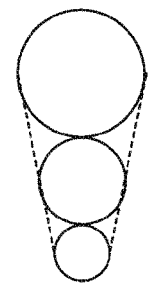 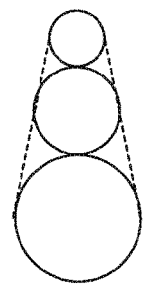
FIG. 6A  FIG. 6B  FIG. 6C  FIG. 6D  FIG. 6E
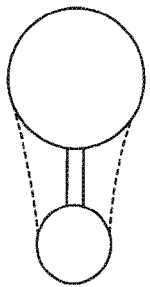 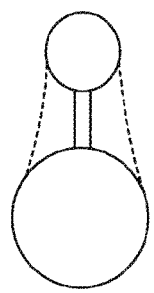
FIG. 6F  FIG. 6G

INTRAGASTRIC BALLOON FOR TREATING OBESITY

BACKGROUND

The present invention is an intragastric device and uses thereof for treating obesity, weight loss and/or obesity-related diseases and, more specifically, to transorally (as by endoscopy) delivered intragastric devices designed to occupy space within a stomach and/or stimulate the stomach wall and react to changing conditions within the stomach.

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States was estimated to be about 400,000 in 2010.

Examples of surgical methods and devices used to treat obesity include the LAP-BAND® (Allergan Medical of Irvine, Calif.) gastric band and the LAP-BAND AP® (Allergan). However, surgery might not be an option for every obese individual; for certain patients, non-surgical therapies or minimal-surgery options are more effective or appropriate.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These devices are designed to provide therapy for moderately obese individuals who need to shed pounds in preparation for surgery, or as part of a dietary or behavioral modification program. These balloons are typically cylindrical or pear-shaped, generally range in size from 200-500 ml or more, are made of an elastomer such as silicone, polyurethane, or latex, and are filled with air, an inert gas, water, or saline.

One such inflatable intragastric balloon is described in U.S. Pat. No. 5,084,061 and is commercially available as the BioEnterics Intragastric Balloon System ("BIB System," sold under the trademark ORBERA). The BIB System comprises a silicone elastomer intragastric balloon that is inserted into the stomach and filled with fluid. Conventionally, the balloons are placed in the stomach in an empty or deflated state and thereafter filled (fully or partially) with a suitable fluid. The balloon occupies space in the stomach, thereby leaving less room available for food and creating a feeling of satiety for the patient. Placement of the intragastric balloon is non-surgical, trans-oral, usually requiring no more than 20-30 minutes. The procedure is performed gastroscopically in an outpatient setting, typically using local anesthesia and sedation. Placement of such balloons is temporary, and such balloons are typically removed after about six months. Removing the balloon requires deflation by puncturing with a gastroscopic instrument, and either aspirating the contents of the balloon and removing it, or allowing the fluid to pass into the patient's stomach. Clinical results with these devices show that for many obese patients, the intragastric balloons significantly help to control appetite and accomplish weight loss.

Some attempted solutions for weight loss by placing devices in the stomach result in unintended consequences. For instance, some devices tend to cause food and liquid to back up in the stomach, leading to symptoms of gastroesophageal reflux disease (GERD), a condition in which the stomach contents (food or liquid) leak backwards from the stomach into the esophagus. Also, the stomach acclimates to some gastric implant devices, leading to an expansion of stomach volume and consequent reduction in the efficacy of the device.

Therefore, despite many advances in the design of intragastric obesity treatment implants, there remains a need for improved devices that can be implanted for longer periods than before or otherwise address certain drawbacks of intragastric balloons and other such implants.

SUMMARY

A transorally inserted intragastric device of the present invention can be used to treat obesity and/or for weight control. The device can do this by causing a feeling or a sensation of satiety in the patient on several basis, for example by contacting the inside or a portion of the inside of the stomach wall of the patient. In addition, preferably the transoral intragastric device allows for easy and quick placement and removal. Surgery is usually not required or is very minimal. In one embodiment, the transoral intragastric device can be placed in the patient's stomach through the mouth and the esophagus and then being placed to reside in the stomach. The transoral intragastric device does not require suturing or stapling to the esophageal or stomach wall, and can remain inside the patient's body for a lengthy period of time (e.g., months or years) before removal.

Each of the disclosed devices is formed of materials that will resist degradation over a period of at least six months within the stomach. The implantable devices are configured to be compressed into a substantially linear transoral delivery configuration and placed in a patient's stomach transorally without surgery to treat and prevent obesity by applying a pressure to the patient's stomach.

In one embodiment, a transoral intragastric device can be used to treat obesity or to reduce weight by stimulating the stomach walls of the patient. The intragastric spring device can be a purely mechanical device comprising a flexible body which in response to an input force in one direction, may deform and cause a resultant displacement in an orthogonal direction, thereby exerting a pressure on the inner stomach walls of the patient.

In another embodiment, a transoral orthogonal intragastric device can include a variable size balloon. The balloon may be configured to occupy volume in the patient's stomach, thereby reducing the amount of space in the patient's stomach.

A still further reactive implantable device disclosed herein has an inflatable body with an internal volumetric capacity of between 400-700 ml and being made of a material that permits it to be compressed into a substantially linear transoral delivery configuration and that will resist degradation over a period of at least six months within the stomach. The body has a central inflatable member and at least two outer wings, and a single internal fluid chamber such that fluid may flow between the central inflatable member and the outer wings. The inflatable body is under filled with fluid such that the outer wings are floppy in the absence of compressive stress on the central inflatable member and stiff when compressive stress from the stomach acts on the central inflatable member. The central inflatable member may have a generally spherical shape along an axis. There are preferably two outer wings extending in opposite directions from the generally spherical inflatable member along the axis. In one form, each of the outer wings includes a narrow shaft portion connected to the central inflatable member terminating in bulbous heads.

An embodiment of the present invention can be an intragastric balloon configured to be implanted transorally into a patient's stomach to treat obesity. Such an intragastric balloon can comprise an inflatable hollow body, the body having a volume which is substantially the same both before and after inflation of the body with a fluid. The body can be made of a material that permits the body to be compressed into a substantially linear transoral delivery configuration, and that will resist degradation over a period of at least six months within the stomach. Additionally, the body can have a single internal chamber with one or more interconnected regions, such that the fluid can flow between each region, the inflatable body being under filled with the fluid such that the once inflated the body is not rigid, thereby having the capability to confirm to the shape of a the stomach. For this intragastric balloon the volume can be between about 300 ml and about 700 ml.

An embodiment of the intragastric balloon disclosed in the paragraph can have three regions, a proximal region for inducing satiety by exerting a pressure on the stomach, a larger central region for inducing satiety by providing a stomach volume occupying effect, and a smaller distal region for anchoring the balloon within the stomach. The intragastric balloon can also have an increased thickness of the distal region shapes for preventing migration of the balloon out of the distal stomach. Additionally, the intragastric can also have in the central region a circumferential ring to for help prevent collapse of the balloon. Furthermore, in the proximal region of the balloon there can be a spine for maintaining the shape of the balloon.

An detailed embodiment of the present invention can be an intragastric balloon configured to be implanted transorally into a patient's stomach to treat obesity, the intragastric balloon comprising: an inflatable hollow body, the body having a volume between about 300 ml and about 700 mls, which volume is substantially the same both before and after inflation of the body with a fluid, wherein the body is made of a material that permits the body to be compressed into a substantially linear transoral delivery configuration, and that will resist degradation over a period of at least six months within the stomach, wherein the body has a single internal chamber with one or more interconnected regions, such that the fluid can flow between each region, the inflatable body being under filled with the fluid such that the once inflated the body is not rigid, thereby having the capability to confirm to the shape of a the stomach, wherein the body has three regions, a proximal region for inducing satiety by exerting a pressure on the stomach, a larger central region for inducing satiety by providing a stomach volume occupying effect, and a smaller distal region for anchoring the balloon within the stomach, wherein the distal region further comprises an increased thickness for preventing migration of the balloon out of the distal stomach, the central region further comprises a circumferential ring for helping preventing collapse of the inflated or deflated balloon, and the proximal region further comprises a spine for helping to maintain the shape of the balloon.

DRAWINGS

The following detailed descriptions are given by way of example, but not intended to limit the scope of the disclosure solely to the specific embodiments described herein, may best be understood in conjunction with the accompanying drawings in which.

Figure 3A:
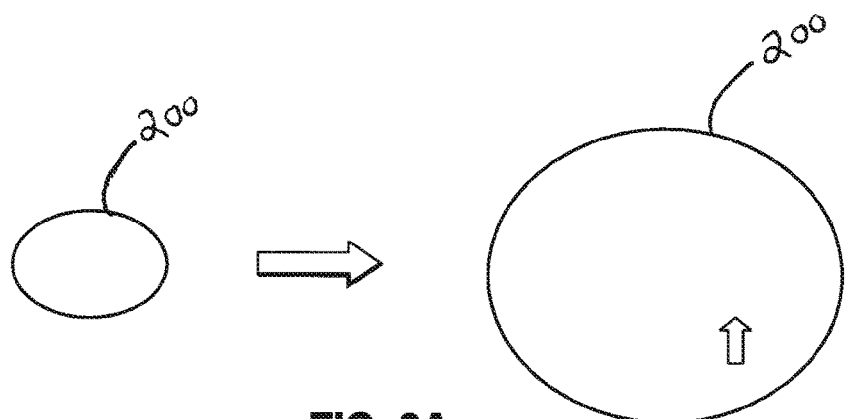

FIG. 3A is diagram illustrating on the left hand side of FIG. 3A an unfilled known intragastric balloon. The right pointing arrow in FIG. 3A represents filling 700 ml of saline into the unfilled intragastric balloon, resulting as shown on the right hand side of FIG. 3A in a balloon shell that is stretched and a balloon that is rigid. The upwards pointing arrow in FIG. 3A represents the high pressure that is exerted by the 700 ml filled balloon onto the inside wall of a patient's stomach by the so filled intragastric balloon. Thus there is a positive differential pressure in the balloon relative to outside of the balloon (i.e. differential pressure>0)

Figure 3B:
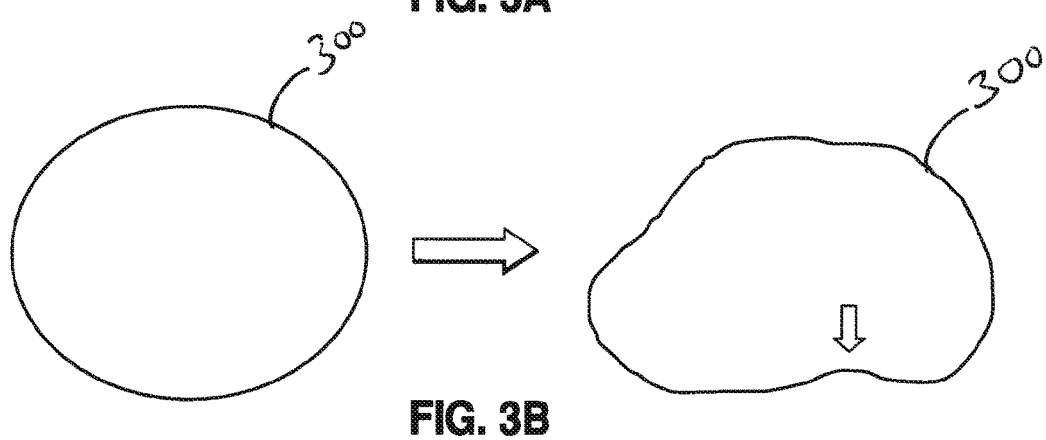

FIG. 3B is a corresponding diagram illustrating on the left hand side of FIG. 3B an unfilled compliant intragastric balloon. The right pointing arrow in FIG. 3B represents filling 700 ml of saline into the unfilled intragastric balloon, resulting as shown on the right hand side of FIG. 3BA in a balloon shell that is under minimal strain and a balloon that is compliant. The downwards pointing arrow in FIG. 3B represents the lower pressure that is exerted by the 700 ml filled compliant balloon, by a differing or amorphous balloon shell shape, onto the inside wall of a patient's stomach by the so filled compliant intragastric balloon. Thus, there exists a zero or negligible differential pressure in the balloon relative to the outside of the balloon (i.e. differential pressure is zero or almost zero)

Figure 4:
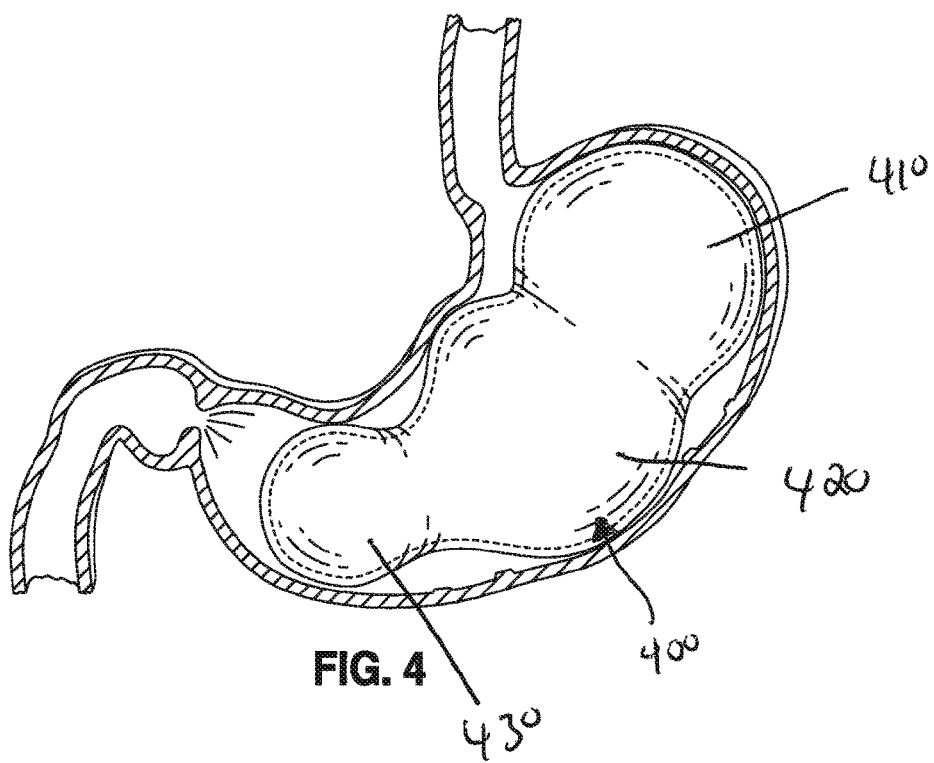

FIG. 4 is an illustrative, perspective view of a saline containing compliant balloon implanted within a patient's stomach, with the proximal (near) stomach wall removed to show the balloon therein.

FIG. 5 is a perspective view of the mandrel (the work piece or mold) over which a liquid polymer (i.e. silicone) dispersion is placed (as by a serial dipping procedure) and then heat cured so as to create the compliant balloon of FIG. 4.

FIGS. 6A to 6G are diagrammatic illustrations of compliant balloon geometries, alternative to those of FIGS. 4 and 5, within the scope of the present invention.

Figure 7:
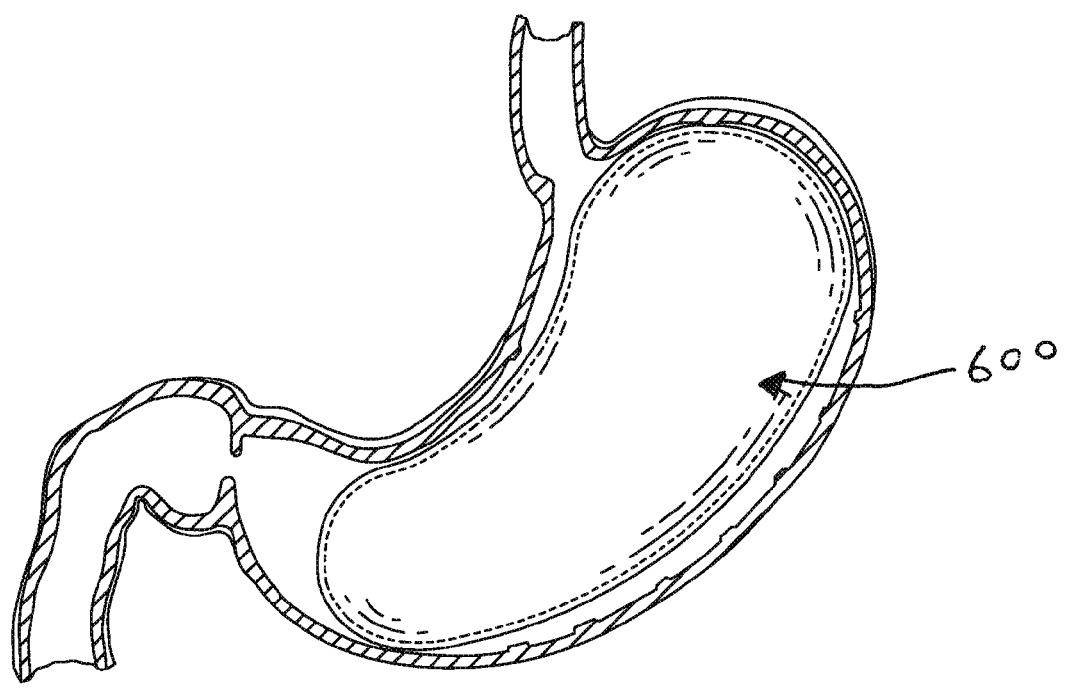

FIG. 7 is an illustrative, perspective view of a further embodiment (kidney shaped), saline containing compliant balloon implanted within a patient's stomach, with the proximal (near) stomach wall removed to show the balloon therein.

FIG. 8A to 8C are diagrammatic illustrations of three further embodiments of compliant balloons within the scope of the present invention.

Figure 9A:
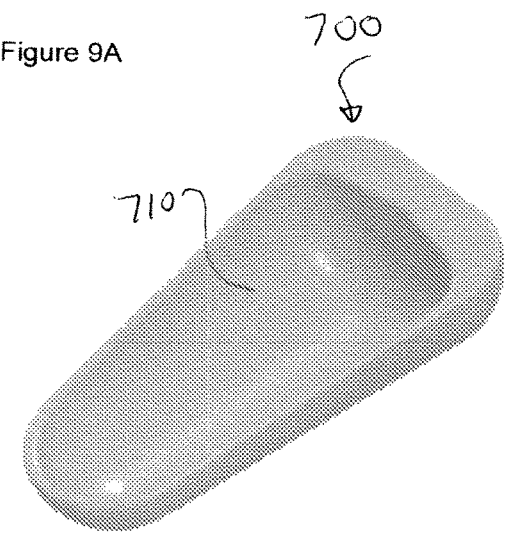

FIG. 9A is a diagram of a mandrel useful for making a further embodiment of the present intragastric balloon.

Figure 9B:
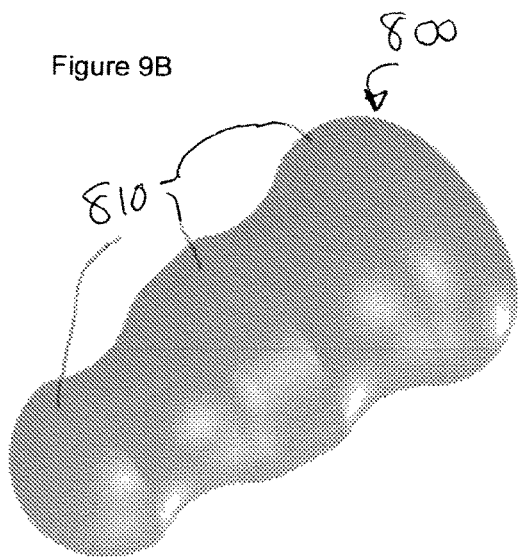

FIG. 9B is a diagram of another mandrel useful for making a further embodiment of the present intragastric balloon.

Figure 9C:
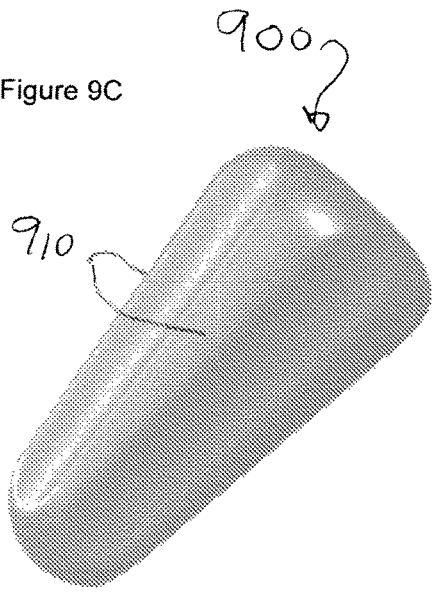

FIG. 9C is a diagram of another mandrel useful for making a further embodiment of the present intragastric balloon.

Figure 9D:
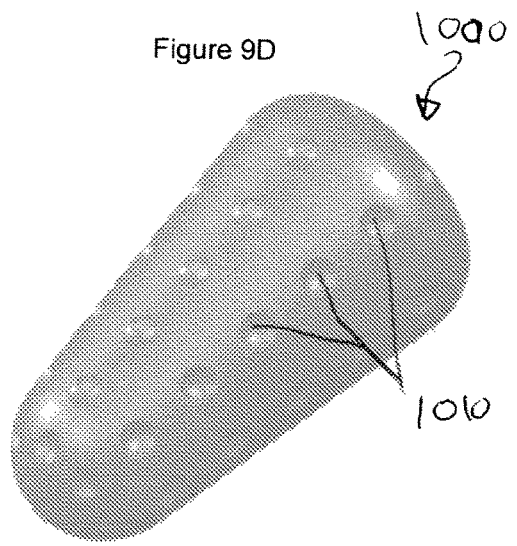

FIG. 9D is a diagram of another mandrel useful for making a further embodiment of the present intragastric balloon.

Figure 10:
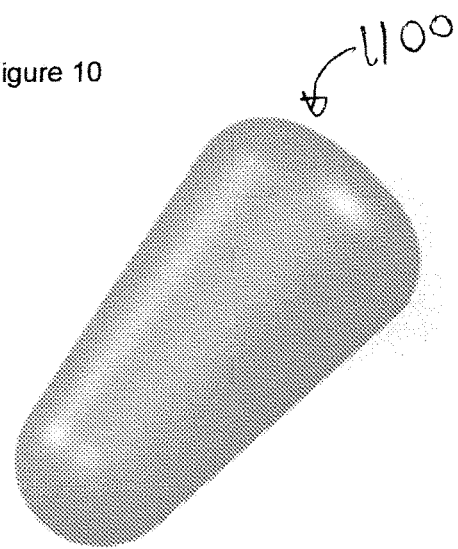

FIG. 10 is a diagram of an inflated intragastric balloon made using the FIG. 9A mandrel.

Figure 11:
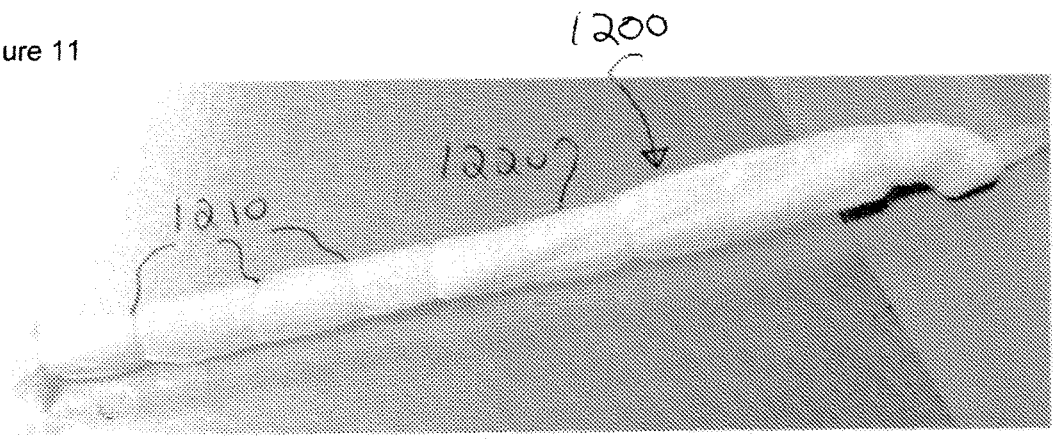

FIG. 11 is a perspective photograph of an intragastric balloon of the present invention enclosed by a novel delivery sheath.

DESCRIPTION

The present invention is based on the discovery that an under filled intragastric balloon can be made to have, once so under filed ("inflated"), a geometry (shape upon inflation) which is flexible or "amorphous", as opposed to having a rigid shape. Unlike the present invention, a rigid upon inflation intragastric balloon does not conform to the shape of the lumen of the stomach into which the balloon is implanted. In one embodiment, an intragastric device described herein can be placed inside the patient, transorally and without invasive surgery, without associated patient risks of invasive surgery and without substantial patient discomfort. Patient recovery time can be minimal as no extensive tissue healing is required. The life span of the intragastric devices can be material dependent and is intended for long term survivability within an acidic stomach environment for a least about six months, although it can be one year or longer.

Figure 1:
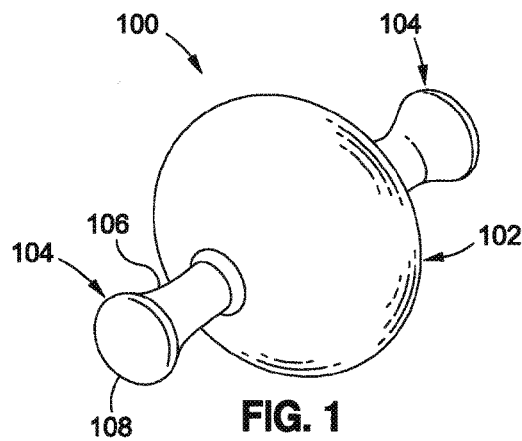
FIG. 1 illustrates a reactive intragastric implant comprising an under filled inflatable member having outer wings that transition between floppy to stiff configurations.

FIG. 1 illustrates a reactive intragastric implant 100 comprising an under filled central inflatable member 102 having outer wings 104 that transition between floppy to stiff configurations. The entire implant 100 defines a single fluid chamber therein. In the illustrated embodiment, the inflatable member 102 is substantially spherical, while the outer wings 104 resemble stems with a narrow proximal shaft 106 terminating in a bulbous head 108. Also, a pair of the outer wings 104 extend from opposite poles of the spherical inflatable member 102, which is believed to facilitate alignment of the implant 100 within the stomach, though more than two such wings distributed more evenly around the inflatable member could be provided.

Figure 2A:
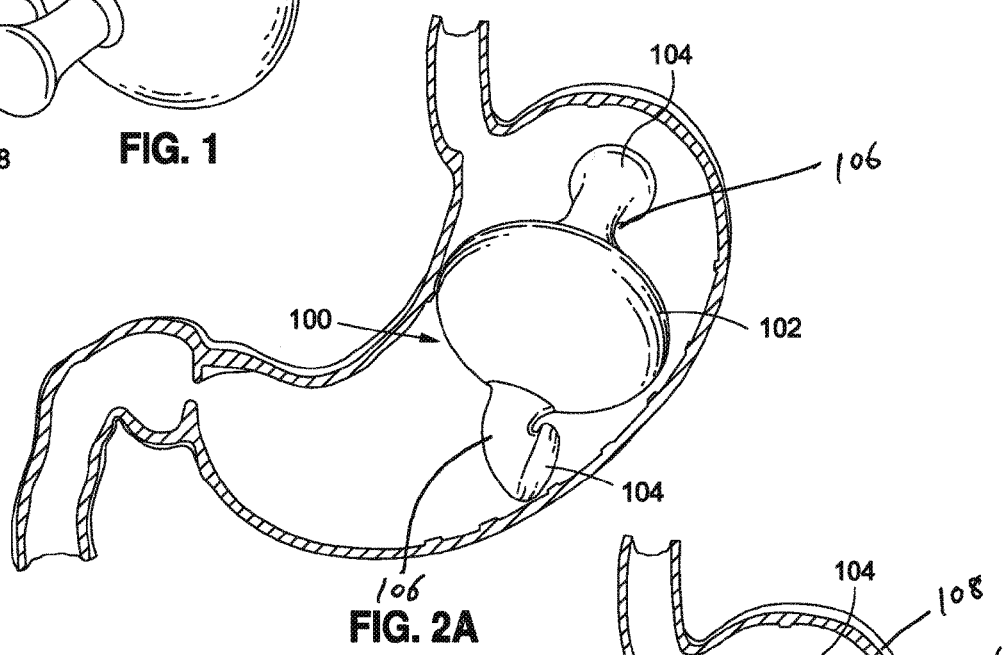
FIGS. 2A and 2B show the intragastric implant of FIG. 1 implanted in the stomach in both relaxed and squeezed states, showing the transition of the outer wings between floppy and stiff configurations.
Figure 2B:
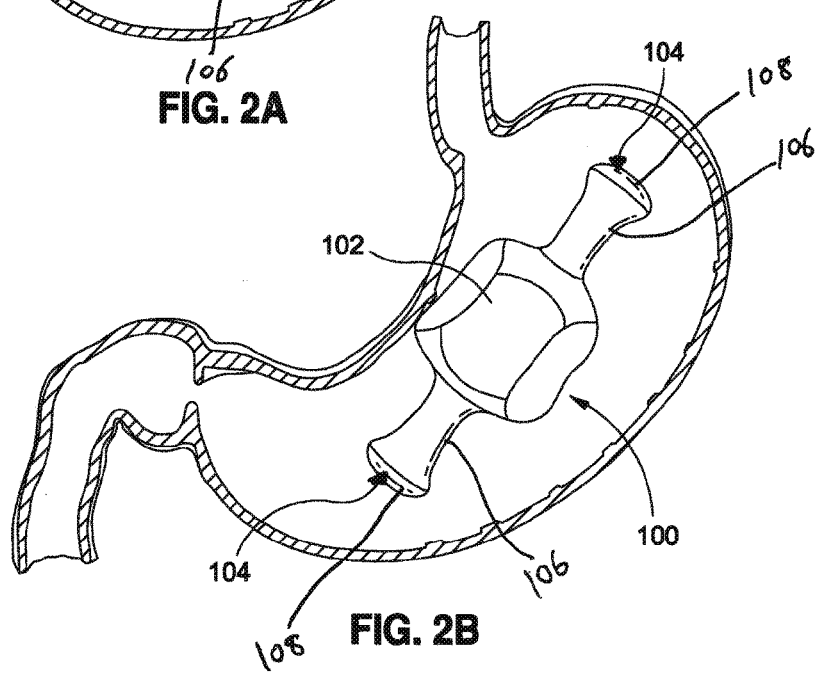

FIG. 2A shows the intragastric implant 100 implanted in the stomach in a relaxed state, while FIG. 2B shows the implant 100 in a squeezed state, illustrating the transition of the outer wings 104 between floppy (FIG. 2A) and stiff (FIG. 2B) configurations. The shape of the central inflatable member 102 in FIG. 2B is a representation of the shape as if squeezed by the surrounding stomach walls, however the illustrated stomach is shown in its relaxed configuration. Transition between the relaxed and squeezed state of the implant 100 occurs when the stomach walls squeeze the central inflatable member 102, thus pressurizing the outer wings 104. In other words, fluid is driven from the central member 102 and into the outer wings 104.

Initially, the entire implant 100 is under filled with a fluid such as saline or air to a degree that the wings 104 are floppy, and a predetermined compressive force causes them to become stiff. For example, the fully filled volume of the intragastric implant 100 may be between 400-700 ml, though the implant is filled with less than that, thus providing slack for flow into the wings 104. Additionally, it should be noted that under filling the implant 100 results in lower stresses within the shell wall, which may improve the degradation properties of the material within the stomach's harsh environment.

It should also be stated that any of the embodiments described herein may utilize materials that improve the efficacy of the implant. For example, a number of elastomeric materials may be used including, but not limited to, rubbers, fluorosilicones, fluoroelastomers, thermoplastic elastomers, or any combinations thereof. The materials are desirably selected so as to increase the durability of the implant and facilitate implantation of at least six months, and preferably more than 1 year.

Material selection may also improve the safety of the implant. Some of the materials suggested herein, for example, may allow for a thinner wall thickness and have a lower coefficient of friction than the implant.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems.

An embodiment of the present invention is an intragastric balloon with a tolerance greater than that of the intragastric balloon shown in FIGS. 1, 2 and 3A. Greater tolerance can be achieved by having a larger allowable amount of variation of a specified quantity, such as in the volume and/or in the shape, of the intragastric balloon of the present invention. Such a greater tolerance intragastric balloon can also be referred to as a more compliant intragastric balloon. A more compliant intragastric balloon can provide many advantages for the treatment of obesity. Thus, known intragastric balloons require the device be filled with from 400 ml to 900 ml of a fluid (typically saline or air) resulting once so filled in an intragastric balloon with a rigid, spherical implant geometry (as in FIG. 3A). Such a geometry can be responsible for one or more of the known post-op (that is after transoral placement [implantation] of the intragastric device into the lumen of the stomach of a patient) adverse effects which can include nausea, intolerance (demanded removal of the device), abdominal pain, vomiting, reflux, and gastric perforation. Thus, when fluid filled, known intragastric devices undergo significant strain, and provide a relatively rigid fluid filled (inflated) balloon.

An intragastric balloon with increased tolerance (compliance) according to the present invention can provide superior gastric volume occupying benefits as compared to a known intragastric balloon, such as the ORBERA™ bariatric intragastric balloon, (available from Allergan UK, Marlow, England), as well as reduced adverse events in the period following device implantation. ORBERA™ is a saline filled silicone balloon that is placed in the stomach of a patient, filled with 400-700 ml of saline, and then left in the stomach for up to six months to provide a feeling of fullness, reduced appetite and weight loss.

An embodiment of the present invention is an intragastric balloon with increased tolerance (a "compliant balloon" therefore) with a shell (a volume holding reservoir), and a valve for inflation. Both parts can be made of silicone or other suitable material and can be implanted and explanted transorally, through the esophagus, and into/out of the stomach during a minimally invasive gastroendoscopic procedure.

Importantly, the compliant balloon of the present invention upon inflation has an amorphous or variable (non-rigid) geometry due to the relationship between the volume of the shell and volume of fluid that is placed into (used to fill) the shell. Additionally, the compliant balloon has a relatively larger and more relaxed silicone shell (as compared to a device such as ORBERA™) thereby making the shell strain and rigidity comparably less than known intragastric balloons (as compared to ORBERA™) which contain the same or a similar fill volume. The increased compliance, with the same volume occupation, provides an improved balloon shape, and the ability of a balloon within the scope of the present invention to readily conform to and/or to contour to individual patient stomach anatomy (that is to the patient's particular internal stomach lumen volume and/or configuration) thereby reducing adverse events upon implantation, while still providing a treatment of obesity. FIG. 3 illustrates a principle or feature of an embodiment of the present invention to show an important difference between a known or standard intragastric balloon 200 (FIG. 3A) and an embodiment of the present compliant intragastric balloon 300 (FIG. 3B). In a standard balloon configuration 200, a smaller initial shell (the left hand side of FIG. 3A) is inflated (eg with a fluid such as saline) which stretches the balloon shell, thereby increasing internal pressure, and creates a rigid sphere, as shown by the right hand side of FIG. 3A. Contrarily, a compliant balloon 300 has a larger initial shell volume (the left hand side of FIG. 3B) and can be inflated to a similar volume, but does not place the shell under major stretch which decreases internal pressure (as compared to the inflated FIG. 3A balloon) and produces an inflated intragastric balloon with an amorphous or irregular shape, as shown by the right hand side of FIG. 3B.

Another embodiment 400 of the present invention compliant balloon (roughly kidney shaped) is shown by FIG. 4, inflated within a stomach. The balloon 400 includes an outer shell having an inner wall surrounding and defining a closed inner chamber. The shell is configured to retain fluid in the chamber. This balloon 400 incorporates three balloon regions: a proximal medium sized region or portion 410, a large central region or portion 420, and a smaller distal region or portion 430. The medium proximal portion 410 provides a balloon shell surface area which contacts and exerts a pressure on the proximal stomach to thereby induce satiety. The larger central portion 420 functions as a stomach space filling region which sterically reduces appetite by preventing ingested food from occupying the same stomach volume. Smallest of the three compliant balloon regions, portion 430 conforms to the more muscular, narrow antrum region of the stomach helping to maintain ("anchor") the balloon within the stoma.

Thus, the embodiment 400 shown in FIG. 4 that has a larger central sphere 420, and is overall kidney shaped. The volume compliance aspect of embodiment 400, as well as it's anatomically more natural geometry provides a device that better conforms to stomach anatomy which providing maximum stomach volume occupation.

FIG. 5 shows a dipping mandrel 500 that can used as a mold to create the balloon 400, using known silicone shell production methods. As shown by FIG. 5, the mandrel 500 has radii (shown by the arrows in FIG. 5) connecting the spheres. The radii can be reduced in size (shorter) to thereby making the portions 410, 420 and 430 more defined (more spherical). Alternately, the radii can be increased (longer) in size to thereby making the portions 410, 420 and 430 less defined (less spherical). Potential benefits of better defined (reduced radii) balloon portions of the implant can include ease of implantation and the filling procedure, or compacting for delivery through the esophagus. Additionally, benefits for less defined (longer radii) balloon portions could include more stomach surface area contact, and fewer stress concentrations on the shell.

An embodiment of the compliant balloon can be modified in any number of ways, while maintaining the core benefits of a compliant balloon, for example for increased conformance of anatomy, reduced shell stresses, reduced patient adverse events, and equivalent gastric volume occupation and FIG. 6 illustrates some, but not all, potential alternatives. Thus FIG. 6 shows seven (A to G) alternative compliant balloon geometries with one or more radii altered. Note the dotted transitions between the individual sections of each design, which represents the variable connecting taper/curve that could be applied between each balloon portion. "Proximal" and "Distal" in FIG. 6 represent how the device would be placed in a patient's anatomy (proximal is closer to head).

FIG. 7 illustrates a kidney shaped embodiment 600 shown within a human stomach. Embodiment 600 has a single balloon shape (only one unity shaped balloon region). Thereby as shown in FIG. 7 permitting embodiment 600 to have close conformance to internal stomach anatomy, without requiring the stomach to reshape (as would be required with a large spherical geometry intragastric balloon). Embodiment 600 is also graphically illustrated in FIGS. 6D and 6F with a tangential shell taper.

Figure 8:
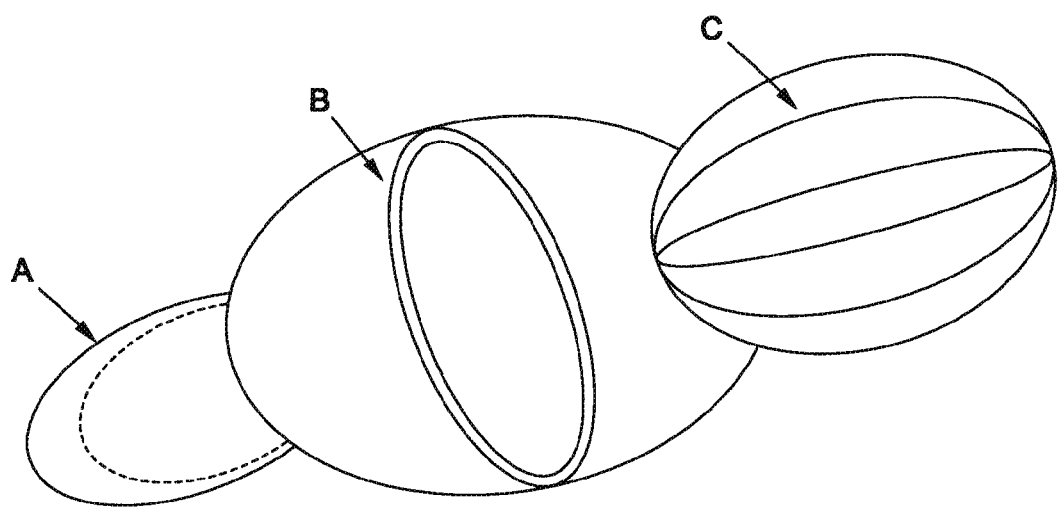

Due to the increased compliance of the device 600, additional features can be applied to the design to prevent, or induce certain physiological and device related occurrences, for example because of the conformity and amorphous shell of device 600, features may be added to prevent premature passing of the device through the pylorus, as shown by FIG. 8. Thus, FIG. 8 shows features that can be added to a compliant balloon within the scope of the present invention to help maintain certain shapes, or prevent unintentional migration into the pylorus: A in FIG. 8 shows increased thickness on the distal balloon segment, which would increase rigidity along the section of device that is most likely to enter the pylorus; B in FIG. 8 shows a circumferential, or series, of rings which would prevent collapse and eventual migration of the device into the duodenum, and; C in FIG. 8 is one of several spines which can help maintain desired balloon shape.

Removal Features

It is known to use for the manufacture of an intragastric balloon a spherically shaped mandrel that is simply a to scale (i.e. scaled) version of the desired final intragastric balloon spherical shape, once inflated. Thus, a spherical intragastric balloon such as Orbera can be made using a similarly spherical mandrel. It has been thought that anatomical (i.e. the shape of the stomach lumen) and endoscopic insertion (i.e. the physical parameters of the esophagus, and ability to insert with patient safety and comfort maintained) requirements dictate use of a spherical intragastric balloon and hence use of a spherical mandrel mandrel. Significantly, we have invented mandrels with non-spherical shapes so that the resulting inflated intragastric balloons have concomitant non-spherical shapes. One benefit of using a non-spherical mandrel is that the resulting intragastric balloon made thereon can retain the shape of the non-spherical mandrel once the intragastric balloon has been deflated, unlike the situation with an intragastric balloon made on a spherical mandrel. An additional benefit of using a non-spherical mandrel is that the resulting non-spherical intragastric balloon can facilitate easy grasping for improved removal of the non-spherical intragastric balloon from the stomach of the patient. Furthermore, use of a non-spherical mandrel also can facilitate easy grasping and improved removal of completed non-spherical intragastric balloon from the mandrel because a spherical mandrel can be difficult to grasp due to the lack of grasping features on the manufactured shell of the spherical intragastric balloon. An embodiment of our non-spherical intragastric balloon shell is much easier to grasp for removal from the mandrel because the shell has folds or other features in the shell that assist grasping.

FIG. 9A to 9D show several non-spherical mandrel embodiments that incorporate features which aid removal of the shell from the mandrel. The geometry of the FIG. 9A to 9D mandrels is such that there exist one or more features of the resulting shell formed on the mandrel which make manipulation or grasping of the balloon much easier, as compared to a spherical intragastric balloon shell made on a spherical mandrel. Thus FIGS. 9A to 9D illustrate mandrel features that create a shell with a fold or fold-like geometry which result in the shell being more readily grasped and removed from the mandrel. Specifically, FIG. 9A is a diagram of a mandrel 700 with a cavity 710 useful for making an embodiment of the present intragastric balloon. FIG. 9B is a diagram of another mandrel 800 useful for making another embodiment of the present intragastric balloon. Mandrel 800 has one or more circular or semi-circular latitudinal ridges 810 to assist grasping and removal of the intragastric balloon formed thereon. FIG. 9C is a diagram of another mandrel 900 useful for making another further embodiment of the present intragastric balloon. Mandrel 900 has one or more circular or semi-circular longitudinal ridges 910 to assist grasping and removal of the intragastric balloon formed thereon. FIG. 9D is a diagram of another mandrel 1000 useful for making another embodiment of the present intragastric balloon. Mandrel 1000 has one or spaced pits 1010 to assist grasping and removal of the intragastric balloon formed thereon.

FIG. 10 is a diagram showing an embodiment 1100 of an inflated intragastric balloon made using mandrel 700.

Barium Integration

Visualization of intragastric balloons in a patient is often done endoscopically. While this offers the greatest visibility, it is also fairly invasive. On the other hand, fluoroscopy or radiographs are far less invasive, but typically provide poor visualization of the lumen of the stomach making eg the intra-stomach lumen location and amount of inflation of the intragastric balloon difficult or impossible to determine. For example using x rays many intragastric balloons being made of thermoplastics and thermoset plastic are difficult to differentiate from surrounding tissue.

To address and resolve these deficiencies of existing visualization methods of an inserted (in the stomach) intragastric balloon visualization we developed intragastric balloons in which a radiopaque substance is incorporated into the shell of the intragastric balloon thereby dramatically improving intra-luminal visualization. Thus, by optimizing the radiopacity of the entire intragastric balloon visualization with minimally invasive x-ray technologies is greatly improved. A suitable radiopaque substance (such as barium sulfate) can be incorporated into the intragastric balloon homogeneously, or it may be incorporated in different amounts in various layers of the shell of the intragastric device. In a particular embodiment because addition of barium sulfate can reduce the GI/stomach acid resistance of the intragastric device shell material, the barium sulfate is incorporated into the inner layer(s) of the intragastric device shell, while leaving the outer layers of the intragastric device shell as more resistant.

Methods of Delivery

The Orbera intragastric device has a silicone sheath. As the Orbera balloon is inflated, the sheath stretches and tears in areas that are pre-cut. Full inflation of the balloon ensures complete deployment of the Orbera balloon and valve from its sheath. With the present compliant intragastric balloon, this same sheath is unsuitable, because the present intragastric balloon is underinflated (relative to mandrel size) so that present intragastric balloon never exerts enough force on the sheath to allow for full deployment. Therefore an alternative intragastric device delivery (insertion) method was developed as set forth below As shown by FIG. 11 one such method developed involves wrapping the intragastric balloon in a sheath 1200 with a suture that is tied in a series of slip knots 1210. A slip string 1220 runs along the length of the fill tube and is long enough to pull from outside the body (after the intragastric balloon is placed in the stomach). Pulling on the string 1220 unties all of the knots 1210 and frees the (uninflated) intragastric balloon in the stomach. The string 1220 is then retrieved from the stomach and the intragastric balloon is filled as usual.

In an alternative embodiment, one can use vision a piece of sheeting that wraps the intragastric balloon. This sheeting can be held closed with a string or some other component that can be activated upon command. Activation of this component (string for example) would loosen the wrap and free the device. The string and wrap could then be retrieved from the stomach.

To summarize, the compliant balloon provides: a soft, compliant implant that is capable of conforming to patient's anatomy while providing gastric volume occupation (i.e. resulting in the patient experience a feeling of fullness); greater patient tolerance of the implant, resulting in reduced recorded post-operative adverse events; low level of strain on the compliant balloons thereby increasing device longevity in the stomach and increased implant durability and resistance to degradation in the gastric environment; reduced patient ulcers and lesions that can be associated with known rigid volume occupying intragastric balloon implants; a low pressure device, as opposed to known intragastric balloons that have increased internal pressure proportional to their fill volume.

EXAMPLE

Example 1: Implantation of a Compliant Balloon

The compliant balloon can be made of a silicone material such as 3206 silicone. Any fill valve can be made from 4850 silicone with 6% $BaSo_4$. Tubular structures or other flexible conduits can be made from silicone rubber as defined by the Food and Drug Administration (FDA) in the Code of Federal Regulations (CFR) Title 21 Section 177.2600. The compliant balloon is intended to occupy a gastric space while also applying intermittent pressure to various and changing areas of the stomach; the device can stimulate feelings of satiety, thereby functioning as a treatment for obesity. The device is implanted transorally via endoscope into the corpus of the stomach using endoscopy. Nasal/Respiratory administration of oxygen and isoflurane is used to maintain anesthesia as necessary.

The compliant balloon within the scope of the present invention can be used for the treatment of obesity as follows. A 45 male patient with a body mass index of 42 who has failed a regime of dieting and exercise, is recalcitrant to oral medication, declines sleeve gastrectomy, or other restrictive GI surgery, has comorbidies including diabetes, high blood pressure and reduced life expectancy sign an informed consent for implantation of the compliant balloon. After an overnight fast, under midazolam conscious sedation (max, 5 mg), endoscopy is performed to rule out any GI abnormalities that would preclude the procedure on the patient. A balloon 400 or 600 is then inserted into the gastric fundus, and 300 ml saline solution is used for balloon inflation, under direct endoscopic vision. The patient remains for 2 hours in the recovery room, to verify full recovery from sedation, before discharge. Weight loss commence almost immediately and the patient reports no nausea, intolerance, abdominal pain, vomiting, or reflux, and no gastric perforation occurs.

An alternate more detailed implant procedure is as follows:

a) Perform preliminary endoscopy on the patient to examine the GI tract and determine if there are any anatomical anomalies which may affect the procedure and/or outcome of the study.
b) Insert and introducer into the over-tube.
c) Insert a gastroscope through the introducer inlet until the flexible portion of the gastroscope is fully exited the distal end of the introducer.
d) Leading under endoscopic vision, gently navigate the gastroscope, followed by the introducer/over-tube, into the stomach.
e) Remove gastroscope and introducer while keeping the over-tube in place. Optionally place the insufflation cap on the over-tubes inlet, insert the gastroscope, and navigate back to the stomach cavity. Optionally, insufflate the stomach with air/inert gas to provide greater endoscopic visual working volume.
f) Collapse the gastric implant and insert the lubricated implant into the over-tube, with inflation catheter following if required.
g) Under endoscopic vision, push the gastric implant down the over-tube with gastroscope until visual confirmation of deployment of the device into the stomach can be determined.
h) Remove the guide-wire from the inflation catheter is used.
i) To inflate using 50-60 cc increments of sterile saline, up to about 300 ml fill volume.
j) Remove the inflation catheter via over-tube.
k) Inspect the gastric implant under endoscopic vision for valve leakage, and any other potential anomalies.
l) Remove the gastroscope from over-tube.
m) Remove the over-tube from the patient.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

All publications cited herein are incorporated herein by reference. Embodiments of the invention disclosed herein are illustrative of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An intragastric balloon configured to be implanted transorally into a patient's stomach to treat obesity, the intragastric balloon comprising:

an inflatable, closed, hollow, compliant body including an outer shell having an inner wall surrounding and defining a closed inner chamber, the closed inner chamber having a volume that is substantially the same both before and after the closed inner chamber is filled with a fluid, wherein, in an implanted state, the closed inner chamber is filled partially with the fluids the body having a proximal end and a distal end opposite the proximal end, the shell being configured to retain the fluid in the closed inner chamber, wherein the body is made of a material that permits the body to be compressed into a substantially linear transoral delivery configuration, and that will resist degradation over a period of at least six months within the stomach, and wherein the closed inner chamber has one or more interconnected regions extending between the proximal and distal ends of the body, such that the fluid can flow freely within the closed inner chamber, the inflatable body filled with the fluid having a fluid volume that is less than the body volume, the body being constructed to conform to the shape of the stomach.

2. The intragastric balloon of claim 1, wherein the fluid volume is between about 300 ml and about 700 ml.

3. The intragastric balloon of claim 2, wherein the shell at the distal region has a greater thickness than the shell at the proximal region to prevent migration of the balloon out of the stomach.

4. The intragastric balloon of claim 2, wherein the body includes a plurality of latitudinal ridges.

5. The intragastric balloon of claim 2, wherein the body includes a plurality of longitudinal ridges.

6. The intragastric balloon of claim 2, wherein the body includes a plurality of spaced pits.

7. The intragastric balloon of claim 1, wherein the body has a plurality of regions including a proximal region and a distal region, and an outer wall of the shell of the body tapers from the proximal region to the distal region.

8. An intragastric balloon configured to be implanted transorally into a patient's stomach to treat obesity, the intragastric balloon comprising:

an inflatable, closed, hollow, non-spherical body including a body shell, the body having a volume between about 300 mls and about 700 mls, which volume is substantially the same both before and after inflation of the body with a fluid, the fluid occupying less than the volume of the body, wherein the body shell is made of a compliant material and is permitted to be compressed into a substantially linear transoral delivery configuration, and that will resist degradation over a period of at least six months within the stomach, wherein the body has a single closed Internal chamber in which the fluid can flow freely, the inflatable body being under-inflated to conform to the shape of the stomach, wherein the body has a proximal region and a distal region, the proximal region larger than the distal region, the proximal region for inducing satiety by exerting a pressure on the stomach, and a smaller distal region for anchoring the balloon within the stomach, wherein the shell at one of the proximal region and the distal region is thicker than the body wall at the other of the proximal region and the distal region.

9. The intragastric balloon of claim 8, wherein the shell of the distal region is thicker than the shell at the proximal region to prevent migration of the balloon out of the stomach.

10. The intragastric balloon of claim 8, wherein the body tapers from the proximal region to the distal region.

11. The intragastric balloon of claim 8, wherein the body is substantially conical in shape.

12. The intragastric balloon of claim 8, wherein the shell includes a plurality of circumferential grooves.

13. The intragastric balloon of claim 8, wherein the shell includes a plurality of latitudinal ridges.

14. The intragastric balloon of claim 8, wherein the shell includes a plurality of longitudinal ridges.

\* \* \* \* \*